(12) United States Patent
Fulgham et al.

(10) Patent No.: US 8,536,220 B2
(45) Date of Patent: Sep. 17, 2013

(54) SUPPLEMENT COMPOSITION AND METHOD OF USE

(76) Inventors: Murray Fulgham, Cleveland, MS (US); Bruce Evans Wofford, Houston, MS (US)

( * ) Notice: Subject to any disclaimer, the term of this patent is extended or adjusted under 35 U.S.C. 154(b) by 143 days.

(21) Appl. No.: 13/012,255

(22) Filed: Jan. 24, 2011

(65) Prior Publication Data
US 2011/0237661 A1  Sep. 29, 2011

Related U.S. Application Data

(60) Provisional application No. 61/298,260, filed on Jan. 26, 2010.

(51) Int. Cl.
*A01N 43/16* (2006.01)
*A61K 31/355* (2006.01)

(52) U.S. Cl.
USPC .......................................................... 514/458

(58) Field of Classification Search
USPC .......................................................... 514/458
See application file for complete search history.

(56) References Cited

U.S. PATENT DOCUMENTS

| | | |
|---|---|---|
| 5,276,056 A | 1/1994 | LeRoy |
| 6,607,745 B2 | 8/2003 | Leneau |
| 7,635,489 B2 | 12/2009 | Leneau |
| 7,658,964 B2 | 2/2010 | Bedding |
| 2010/0112187 A1* | 5/2010 | Crank ........................... 426/656 |
| 2011/0171187 A1* | 7/2011 | Moore et al. ................ 424/93.51 |

* cited by examiner

*Primary Examiner* — Yong Chong
(74) *Attorney, Agent, or Firm* — Harris, Shelton, Hanover & Walsh

(57) ABSTRACT

The present invention relates to a dietary supplement composition made of: linolinic expeller pressed soybean oil in the range of 65%-85%, Omega 3 (18/12) fish oil 15%-35%, and 1%-20% alpha-tocopherol and a method to use this composition to supplement the diet of a domestic animal, such as a canine or an equine.

6 Claims, No Drawings

SUPPLEMENT COMPOSITION AND METHOD OF USE

RELATED APPLICATIONS

This application incorporates by reference in its entirety and claims priority under 35 U.S.C. Section 119(e) to U.S. provisional patent application Ser. No. 61/298,260 filed Jan. 26, 2010 (hereby incorporated by reference).

FIELD OF THE INVENTION

The present invention is related to an animal nutritional supplement and, more particularly to a method of using an equine nutritional supplement to alleviate chronic or acute conditions in domestic animals such as equines and canines

BACKGROUND OF THE INVENTION

Equines are known to suffer from a number of conditions related to vitamin and minerals deficiencies due to poor quality forage or hay, chronic colic, chronic diarrhea, or anorexia resulting from dental disease. In addition, there may also be disturbances in absorption as the result of liver or biliary tract disease, hypothyroidism, anemia and other pathological conditions of the digestive system and related organs. Numerous equine supplements are currently on the market. Some of these supplements include various Omega 3 products. The Omega 3 is from a variety of sources, strengths, and types of Omega 3 that supply EPA, DHA or ALA for supplementation of the equine diet. Some are from marine oils such as fish oil which contain different amounts of DHA and EPA, the long chain Omega 3s, depending on which fish and which part of the ocean they came from. Some come from vegetable oils such as soybean oil, canola oil, or flax seed, all of which contain ALA Omega 3, the parent chain of Omega 3. However, the equine diet in the wild provides a balance of Omega 3, Omega 6 and Omega 9. Domestic animals feeds may disturb this balance and result in chronic or acute conditions.

SUMMARY OF THE INVENTION

Thus, it is a purpose of the present invention to provide a nutritional supplement for alleviating various chronic or acute conditions in domestic animals associated with an imbalance of Omega 3, Omega 6 and Omega 9. It is also a purpose of the present invention to provide a method of use for the nutritional supplement, of the present invention, to alleviate chronic or acute conditions in domestic animals.

In accordance with a preferred embodiment of the invention, an equine nutritional supplement for improving omega balance in domestic animals is made of: a balance of Omega 3, Omega 6, and Omega 9 plus other nutrients in expeller pressed soybean oil. More specifically, this composition is made of: linolenic expeller pressed soybean oil in a volume range of 65%-85%, Omega 3 fish oil in the range of 15%-35%, and 1%-20% alpha-tocopherol (natural vitamin e). This invention further provides a method for alleviating chronic or acute conditions in animals by the method of administering a nutritional supplement to the animal.

This invention more specially provides a method for alleviating anhidrosis in an equine. This method involves administering a nutritional supplement composition made of 3:1 omega 6 to omega 3 and 12,000 IU per serving of alpha-tocopherol.

DETAILED DESCRIPTION OF THE INVENTION

The present invention relates to a nutritional supplement to balance the distribution of Omega 3s, Omega 6s, and Omega 9 in the diet of a domestic animal. The present invention relates to a composition made of: linolenic expeller pressed soybean oil in the range of 65%-85%, Omega 3 fish oil in the range of 15%-35%, and 1%-20% alpha-tocopherol (natural vitamin e). In the preferred embodiment, the fish oil is 18/12. More specifically, the parent chain (ALA) of Omega 3s from natural expeller pressed soy oil and the long chain Omega 3s (DHA and EPA) from natural Omega 3 fish oil and natural alpha-tocopherol (vitamin E) are provided. The alpha-tocopherol has a dual role in providing the needed additional vitamin E and acting as a preservative for this composition. The alpha-tocopherol is in a concentration from between 3000 to 28,000 IU per serving.

Linolenic expeller pressed soybean oil is made by mechanical (expeller) extraction. During mechanical extraction, an expeller press crushes the soybeans to extract the oil. This pressing is done under intense pressure, and raises the temperature of the oil to 185 to 200° F. (85-93.3° C.). Typically, the soybeans are heated up to 250° F. (120° C.) before being placed in the expeller. Alternatively, the linolenic expeller pressed soybean oil can be cold pressed using filtration and distilled water to filter the oil.

The linolenic expeller pressed soybean oil is admixed with the fish oil and alpha-tocopherol in the volume range of 65%-85%, Omega 3 (18/12) fish oil in the range of 15%-35%, and 1%-20% alpha-tocopherol (natural vitamin e) to form the supplement composition of the present invention.

Bulk Fish Oil comes in two general varieties: 18% EPA, 12% DHA and 30%. Both refer to the general level of omega-3 in the oil. In 18/12 the levels of EPA and DHA are set in the specifications to 18% EPA and 12% DHA. In what is generally considered a lower grade (30% fish oil) the levels of EPA and DHA are not specified and therefore, depending on seasonal variations.

The animal nutritional supplement can be used for improving or alleviating various chronic or acute conditions in equine or canines associated with an imbalance of Omega 3, Omega 6 and Omega 9. The use of the supplement composition has been show to provide: a healthy digestive system, reduces inflammation in the joints, blocks lactic acid buildup in muscles, increases blood flow to all organs and joints promotes beautiful hair coats and healthy hooves, builds a strong immune system and promotes a healthy reproductive system. The serving size of the present composition for an average horse is 4 ounces daily. (1 oz. per 300 lbs.) It is dispensed directly onto feed. If the horse is feed twice daily the dosage can be applied either in one feeding or divided in two and given at both feedings. Serving size can be increased for horses with specific needs or problems. The composition can be formulated as an equine top dress liquid mixture by packaging the liquid product in a gallon container.

In an alternative embodiment, the composition can be provided as an additive to an equine feed. In another embodiment, the supplement composition can be prepared as a solid supplement. In this embodiment, the supplement composition can be blended with inactive ingredients such as: natural soy lecithin, apple pectin, calcium carbonate, dicalcium phosphate, citric acid, flavoring, anise oil, primary yeast dehydrated, silicon dioxide, yeast extract, yeast fermentation solubles, vegetable stearate, and lignin sulfate. The inactive ingredients can be added to then extent they do not change the fundamental properties of the supplement composition. The solid supplement composition can be formulated into pellets according to techniques know to those skilled in the art.

In an alternative embodiment, a nutritional supplement composition is made linolinic expeller pressed soybean oil to Omega 3 fish oil is ratio of 3:1 and alpha-tocopherol (natural vitamin e). Sufficient alpha-tocopherol is added to the mixture to provide 12,000 IU per serving of alpha-tocopherol. This nutritional supplement composition can be used to treat anhidrosis in equines. Equine anhidrosis is the inability in a horse to sweat due to intolerance to heat and humidity. It is estimated that 20%-30% of horses in southern regions suffer sweat disorders (anhidrosis). Horses raised in cool climates and later transferred to very warm southern or tropical areas are prone to this illness.

EXAMPLE 1

Equine A 2 yr. old western pleasure horse received four oz. of the composition on a daily basis for eight weeks. After receiving the supplement, it was observed that equine A was quieter and more focused on his training than ever before. The weight gain and bloom within the first month were incredibly. Equine B a young horse with early onset of arthritis received the composition for its anti-inflammatory benefits. It was reported by the attending veterinarian that the product added weight and bloom on horses quickly and did not affect their energy levels, in contrast to prior supplements.

EXAMPLE 2

In August, 2010, Equine C could barely stand due to pain. The horse was diagnosed with navicular syndrome, i.e. heel soreness or lameness. With this condition, some horses may be sound with large structural navicular changes whereas others may be extremely lame with minimal radiographic changes. The most commonly seen changes are enlarged blood vessel channels, "lollipop lesions", spurring, tiny fractures off the navicular edge, cystic or lytic areas within the bone, and erosion of the contact area between the navicular bone and deep digital flexor tendon. Equine C was treated with four oz. of the composition on a daily basis for 12 weeks crossed with the Acuscope/Myoscope treatments. Equine C is now pain free and able to work.

EXAMPLE 3

Four oz. the alternate composition of this invention was given on a daily basis was given to Equine group D for anhidrosis for 60 days. An immediate improvement in the ability to sweat was observed. Additionally, the overall condition of Equine group D improved within a few short weeks. The improvements in condition included reduced swelling, the ability to hold their weight better and their hooves and hair coats seemed to have improved as well.

EXAMPLE 4

Canine A was misdiagnosed with allergies in early June, 2010 and the treatment of antibiotics and steroids sent her into a severe downward spiral. Her condition was diagnoses as deimadex mange, which all puppies carry from their mothers at birth. A healthy immune system keeps puppies from having trouble with these mites. Her immune system was basically shut down from the treatment. Her condition worsened. Her skin was red, and hair was falling out. Canine A was treated with IMMUNEPLEX, derma support herbal remedies and the present composition at ½ ounce per day. Within a week, whiskers of hair appeared and her hair and skin were restored to normal. Canine A has received the treatment continuously since to maintain healthy skin and coat.

Although the present invention has been described and illustrated with respect to a preferred embodiment and a preferred use therefore, it is not to be so limited since modifications and changes can be made therein which are within the full intended scope of the invention.

The invention claimed is:

1. A method for alleviating chronic or acute conditions in a domestic animal, the method comprising administering a nutritional supplement to said domestic animal, the nutritional supplement consisting of linolenic expeller pressed soybean oil in the volume range of 65%-85%, Omega 3 fish oil 15%-35%, and 1%-20% alpha tocopherol (natural vitamin e), as the only active ingredients in the nutritional supplement, wherein the chronic or acute conditions are selected from the group consisting of arthritis, lameness, anhidrosis, and mange.

2. The method of claim 1 wherein said domestic animal is an equine.

3. The method of claim 2 wherein 1 oz. said nutritional supplement is administered per 300 lbs of said equine per day.

4. The method of claim 3 wherein the concentration of alpha-tocopherol ranges from 3000-28,000 IU per day.

5. The method of claim 1 wherein said domestic animal is a canine.

6. The method of claim 5 wherein 1 oz. said nutritional supplement is administered per 50 pounds of canine per day.

* * * * *